United States Patent [19]
Kessel

[11] Patent Number: 5,958,200
[45] Date of Patent: Sep. 28, 1999

[54] ELECTROCHEMICAL GAS SENSOR

[75] Inventor: Robert Kessel, Bad Oldesloe, Germany

[73] Assignee: Drägerwerk AG, Lübeck, Germany

[21] Appl. No.: 08/965,255

[22] Filed: Nov. 6, 1997

[30] Foreign Application Priority Data

Apr. 23, 1997 [DE] Germany ............................ 197 17 056

[51] Int. Cl.$^6$ ................................................ G01N 27/404
[52] U.S. Cl. ........................ 204/415; 204/431; 205/782.5
[58] Field of Search ..................................... 204/415, 431, 204/432, 430; 205/782, 782.5, 783, 788

[56] References Cited

U.S. PATENT DOCUMENTS

| | | | |
|---|---|---|---|
| 2,830,945 | 4/1958 | Keidel ..................................... | 204/430 |
| 2,934,693 | 4/1960 | Reinecke et al. ....................... | 204/430 |
| 4,967,295 | 10/1990 | Yamauchi et al. ..................... | 360/97.2 |
| 5,346,604 | 9/1994 | Van Sin et al. ......................... | 204/415 |
| 5,346,605 | 9/1994 | Wolcott et al. ......................... | 204/415 |

OTHER PUBLICATIONS

*Handbook of Chemistry and Physics*, 55th Ed., (1974), pp. B–78, B–103, B–117, B–121, B–139 Month Unavailable.

Primary Examiner—T. Tung
Attorney, Agent, or Firm—McGlew and Tuttle, P.C.

[57] ABSTRACT

The present invention pertains to an electrochemical gas sensor, which has an electrode system for the measurement and is directly coupled with the environment via a gas inlet. To avoid fault liability and incorrect measurements in the case of rapid changes in atmospheric humidity, a moisture reservoir is provided according to the present invention at the gas inlet, and the moisture reservoir is designed to reversibly exchange moisture with the gas atmosphere surrounding it, following the relative humidity of the gas atmosphere, in order to buffer or damp variations in the relative humidity of the gas atmosphere acting on the electrode system. The moisture reservoir may have, e.g., a container body, whose walls have moisture-permeable areas, which face the gas atmosphere in the gas sample volume or the gas diffusing into it, and in which hygroscopic substances are contained. For example, salt solutions, highly concentrated acids or silica gel, which extract moisture from the environment when the humidity of the ambient air increases and release the moisture when the humidity of the ambient air decreases, may be contained in the container body.

17 Claims, 2 Drawing Sheets

ELECTROCHEMICAL GAS SENSOR

FIELD OF THE INVENTION

The present invention pertains generally to electrochemical gas sensors which are directly coupled with the ambient atmosphere via a gas inlet. The gases entering can interact with an electrode system in an electrolyte, which is typically separated from the gas phase by a diaphragm to obtain an electrochemical measurement of the concentration of a certain gas.

BACKGROUND OF THE INVENTION

Gas sensors of this type have been known in many different forms and have been used for various applications, in chemical production plants, laboratories and plants in which gases are used as operating materials, for monitoring, control or as an alarm.

One problem that arises in connection with such electrochemical gas sensors is that changes in the humidity of the ambient atmosphere may lead to changes in the value of the measured signal and especially to a variation in the zero signal of the gas sensor, in the signal value that is furnished by the gas sensor when the concentration of the gas being measured in the ambient atmosphere is zero. If there are variations in the zero signal in the case of changes in the ambient humidity, an excessively high or excessively low measured gas concentration may be erroneously mimicked, which may lead to the triggering of false alarms or to the suppression of states of alarm when an alarm should have actually been triggered. The problems being described here, which are caused by the measured signal being affected by changes in the humidity of the ambient air, are especially pronounced in the case of rapid changes in humidity and they subside thereafter over time.

Prior-art filters are not particularly suitable for handling these problems, because they are consumed rapidly because of seasonal and weather-related variations in humidity and therefore they would have to be replaced frequently.

SUMMARY AND OBJECTS OF THE INVENTION

The object of the present invention is to provide an electrochemical gas sensor, which responds less sensitively to rapid changes in the humidity of the ambient atmosphere.

According to the invention, an electrochemical gas sensor is provided which has an electrode system and a gas inlet, with which the gas sensor is directly coupled with the environment. A moisture reservoir is provided which reversibly exchanges moisture with the gas atmosphere surrounding the reservoir. This follows the relative humidity of the gas atmosphere, in order to buffer variations in the relative humidity of the gas atmosphere acting on the electrode system. The moisture reservoir is arranged at the gas inlet.

The gas sensor is provided according to the present invention with the moisture reservoir arranged at the gas inlet of the gas sensor follows or tracks the relative humidity of the gas atmosphere surrounding it. The reservoir is able to reversibly exchange humidity with that gas atmosphere. In this way it acts as a buffer or attenuator as to the variations in the relative humidity of the gas atmosphere acting on the electrode system. The moisture reservoir is intended to reach a state of equilibrium with the gas atmosphere surrounding it with respect to the humidity. If the humidity in the gas atmosphere is increasing, moisture is at first extracted from the surrounding gas atmosphere in order for the moisture reservoir to be able to reach the state of equilibrium with increased humidity by taking up moisture, whereas, conversely, the moisture reservoir releases moisture when the humidity of the gas atmosphere is decreasing in order to reach a state of equilibrium with lower humidity. Therefore, the moisture reservoir seeks to locally counteract changes in humidity and it increases, so to speak, the inertia of the gas atmosphere around the electrode system regarding to changes in humidity. As a result, the moisture reservoir dampens the variations in the humidity of the gas atmosphere acting on the electrode system over time, i.e., a retarded, slow establishment at a new humidity level is achieved. Disturbances and effects on the value of the measured signal of the electrochemical gas sensor are minimized as a result, because such effects occur mainly during rapid changes in humidity and subside over time.

The moisture reservoir may have, e.g., a container body which has wall areas permeable to moisture and in which hygroscopic substances are contained. The hygroscopic substances extract moisture from the environment until a sufficient amount of moisture is stored and a state of equilibrium is reached. If the humidity drops again in the ambient atmosphere, part of the moisture being stored is again released. The hygroscopic substances in question may be, e.g., solutions of the salts LiCl, LiBr, etc., and highly concentrated acids ($H_2SO_4$, $H_3PO_4$). The salt solutions should not be completely saturated, but they should preferably have such a concentration that the solution can reach an equilibrium with the humidity of the air in the practically relevant humidity range of, e.g., 5 to 95%. One example of a salt solution that can be used in practice with the present invention is a 6-molar LiCl solution. As an alternative to a container body, in which hygroscopic substances are contained in the liquid form, it is also possible to use as the moisture reservoir a solid, e.g., one consisting of silica gel or a porous plastic, which are able to absorb and store moisture.

A moisture reservoir with a container body shall be dimensioned such that the container body shall have a sufficient storage capacity to take up the moisture necessary for reaching the state of equilibrium in a humidity range desired for the use, e.g., between 5 and 95% relative humidity. If a salt solution is used in a container body, this means in practice that the salt solution fills the container body only partially at an average humidity, so that a sufficient uptake volume is left to take up in the solution a sufficient amount of moisture, which is necessary for reaching the state of equilibrium, at high humidity in the air.

The present invention will be explained below based on exemplary embodiments.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
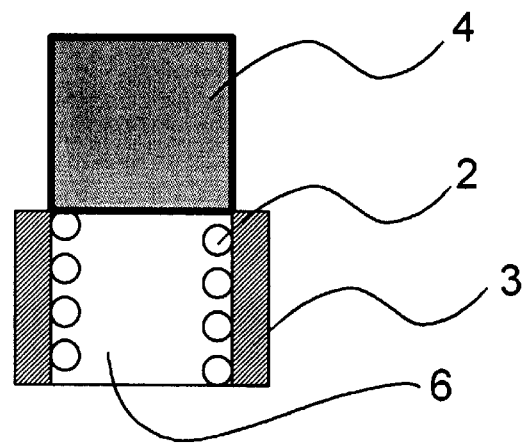
FIG. 1 is a side view of a first embodiment of the gas sensor with moisture reservoir.

Referring to the drawings in particular, the invention comprises a gas sensor 4 which is shown only schematically in FIG. 1. In the representations shown in the figures, the housing of the gas sensor 4 has a gas inlet at the bottom, through which the gas can enter the electrode system gas sensor 4 from the ambient atmosphere and act on the electrode system. A moisture reservoir is arranged at the housing of the gas sensor 4. In this embodiment, the moisture reservoir is a tube 3 made of a material impermeable to water and a flexible tube 2 made of a porous material permeable to moisture, which is placed inside the tube 3 in a helical pattern and is fastened. The tube 3 defines a gas diffusion path 6, over which the gas from the ambient atmosphere must pass to reach the gas sample volume of the gas sensor 4 through the gas inlet. The flexible tube 2 at the inner wall of the tube 3 is filled with a hygroscopic substance such that the flexible tube is able to absorb moisture from the gas atmosphere in a desired relative humidity range, e.g., between 5 and 95%, in order to reach the state of equilibrium.

The moisture reservoir, especially the length of the tube 3 and of the flexible tube 2 of the container body, shall be dimensioned such that its storage capacity shall be sufficient to reach the desired inertia, with which the relative humidity in the gas sample volume becomes established at a new ambient value. In typical applications, the internal diameter of the tube 3 may be, e.g., 20 mm. The flexible tube 2 may be, e.g., a flexible tube made of porous PTFE material, with a diameter of, e.g., 5 mm. The length of the tube 3 and of the flexible tube 2 determine, together with the amount and the effectiveness of the hygroscopic substance in the flexible tube, the effectiveness of the moisture reservoir. The longer the tube 3 and the flexible tube 2 and the larger the total amount of hygroscopic substance that is thus present, the more effectively can a change in the ambient humidity be buffered, i.e., the more sluggishly will the humidity in the gas sample volume of the gas sensor follow the changing ambient air humidity conditions.

Figure 2:
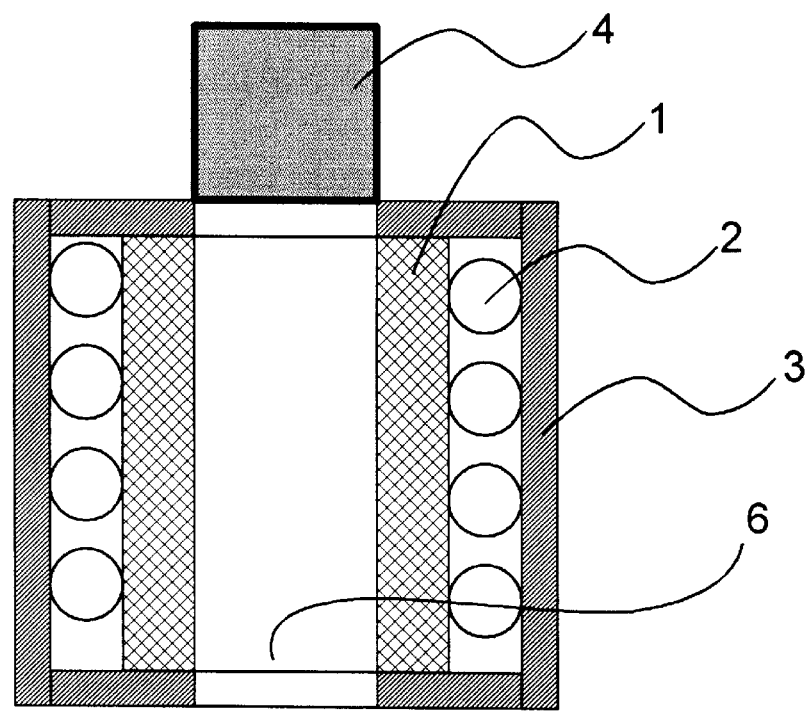
FIG. 2 is a side view of a second embodiment of the gas sensor with moisture reservoir.

In the embodiment according to FIG. 2, the moisture reservoir is shown with a container body, which has a water-impermeable tube 3 with flanges at its ends as well as a porous, moisture-permeable inner tube 1, which surround a central gas diffusion path 6. A flexible tube 2 made of a porous, moisture-permeable material is arranged in a helical pattern in the intermediate space between the two tubes 1 and 3. The flexible tube 2 contains, in turn, as in the first exemplary embodiment, a hygroscopic substance, e.g., one of the salt solutions (i.e., solutions of the salts LiCl, LiBr, etc., e.g 6-molar LiCl solution) or a highly concentrated acid (i.e. $H_2SO_4$, $H_3PO_4$).

The porous inner tube 1 may be formed by, e.g., a porous PTFE tube with an internal diameter of 28 mm, a wall thickness of 2 mm, and a length of 100 mm. A flexible tube may be wound, as described above, around the porous inner tube 1 in a helical pattern. Solid plastic materials may be used as the outer water-tight tube 3 of the container body, but it is also possible to use flexible forms, e.g., a shrinkdown tubing, which seals the moisture-permeable flexible tube 2 in a water-tight manner to the outside, so that moisture can be transported into the gas diffusion path 6 or in the opposite direction through the porous inner tube 1 only.

Figure 3:
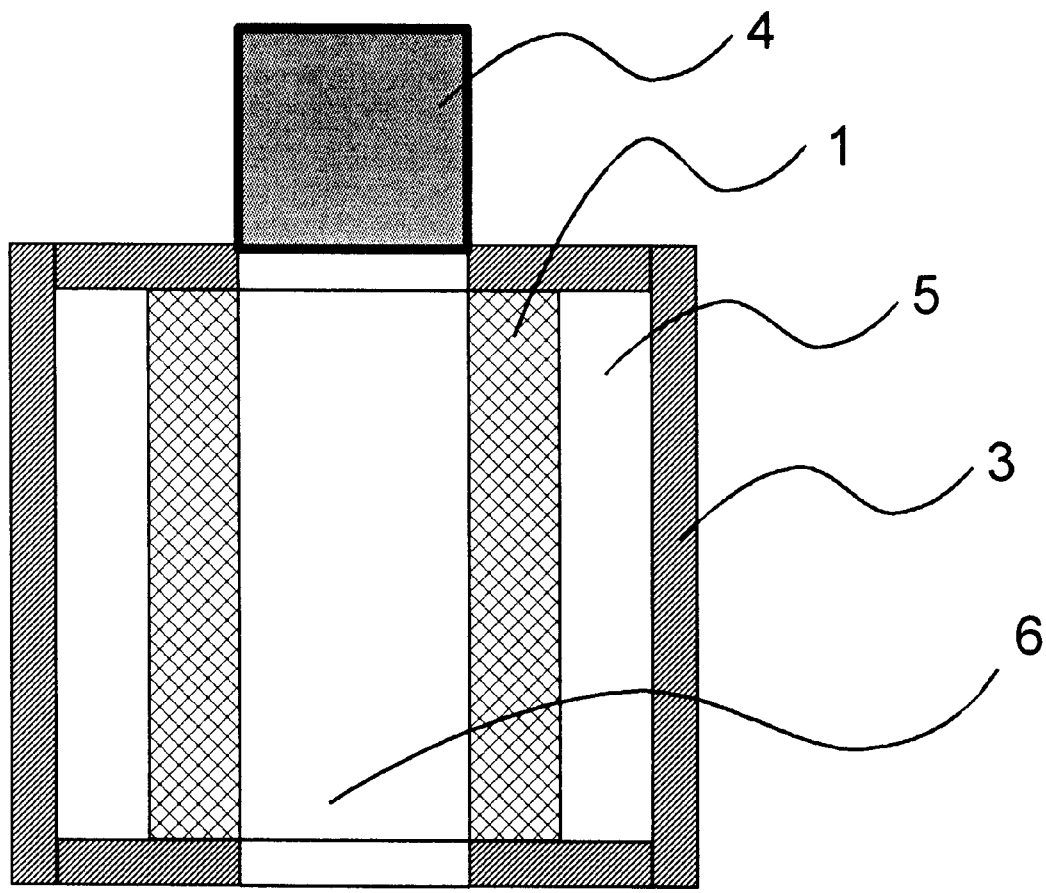
FIG. 3 is a side view of a third embodiment of the gas sensor with moisture reservoir.

The third exemplary embodiment shown in FIG. 3 differs from that shown in FIG. 2 only in that the moisture-permeable flexible tube was abandoned. The hygroscopic substance is accommodated, instead, directly in the intermediate space 5 between the water-tight tube 3 and the inner, moisture-permeable tube 1, and the intermediate space is closed by end flanges at the opposite ends of the water-impermeable tube 3.

The gas diffusion path 6 is designed as a path extending linearly toward the gas sensor 4 in the embodiments shown. The gas diffusion path could, in principle, also be designed such that the gas flows laterally through the outer area 3 of the container body, the interior of the container body and through the moisture-permeable inner wall area 1 to the central gas diffusion path, in which case the outer end of the gas diffusion path 6 could be closed.

In an alternative embodiment, the moisture reservoir may be designed such that it covers the gas inlet or fills out the cross section of the gas diffusion path. Gas entering the gas sensor must diffuse in this case through the moisture reservoir to reach the electrode system. Such a design shall be preferred for gases that are characterized by only a weak tendency to be adsorbed on solid surfaces, e.g., phosphine.

While specific embodiments of the invention have been shown and described in detail to illustrate the application of the principles of the invention, it will be understood that the invention may be embodied otherwise without departing from such principles.

What is claimed is:

1. An electrochemical gas sensor, comprising:
   an electrode system;
   a gas inlet, with which the electrode system is directly coupled with the environment;
   moisture reservoir means for reversibly exchanging moisture with a gas atmosphere surrounding said reservoir means, said moisture reservoir means has a container body with walls having moisture-permeable areas and hygroscopic substances contained in said body, said container body has a gas diffusion path arranged at the gas sensor such that said gas diffusion path communicates with said electrode system, wherein said moisture-permeable areas surround said gas diffusion path.

2. The electrochemical gas sensor in accordance with claim 1, wherein said container body includes a tube made of a water-tight material and a flexible tube made of a moisture-permeable material extending at an inner wall of said tube and containing said hygroscopic substances in an aqueous solution.

3. The electrochemical gas sensor in accordance with claim 1, wherein said container body has a hollow body made of a water-tight material, said hollow body containing said hygroscopic substances.

4. The electrochemical gas sensor in accordance with claim 3, wherein a flexible tube made of a moisture-permeable material contains the hygroscopic substances in an aqueous solution, and is arranged inside said hollow body.

5. The electrochemical gas sensor in accordance with claim 1, wherein silica gel is present in said moisture reservoir means.

6. The electrochemical gas sensor in accordance with claim 1, wherein an aqueous salt solution is present in said moisture reservoir means.

7. The electrochemical gas sensor in accordance with claim 6, wherein said salt comprises at least one of LiCl, LiBr, $K_2CO_3$, $Ca(NO_3)_2 4H_2O$, $NH_4NO_3$ and $NaNO_2$.

8. The electrochemical gas sensor in accordance with claim 1, wherein a highly concentrated acid is contained in the moisture reservoir means.

9. The electrochemical gas sensor in accordance with claim 8, wherein said highly concentrated acid is $H_2SO_4$ or $H_3PO_4$.

10. The electrochemical gas sensor in accordance with claim 1, wherein said moisture reservoir means is formed by a porous solid, which is able to take up and store moisture.

11. The electrochemical gas sensor in accordance with claim 1, wherein the moisture reservoir means is formed by a body containing hygroscopic substances, which covers the gas inlet, so that the gas entering the gas sensor must diffuse through the moisture reservoir.

12. An electrochemical gas sensor, comprising:

an electrode system for generating a signal corresponding to a concentration of a gas in an atmosphere;

a gas diffusion path through which said electrode system communicates with the atmosphere;

moisture reservoir means for reversibly exchanging moisture with a portion of the atmosphere in said gas diffusion path, said moisture reservoir means surrounds said diffusion path.

13. An electrochemical gas sensor, comprising:

an electrode system for generating a signal corresponding to a concentration of a gas in an atmosphere;

a gas diffusion path through which said electrode system communicates with the atmosphere;

moisture reservoir means for reversibly exchanging moisture with a portion of the atmosphere in said gas diffusion path, said moisture reservoir means includes an inner wall and an outer wall, said inner wall being moisture-permeable.

14. An electrochemical gas sensor in accordance with claim 13, wherein:

a helically wound tube formed of material permeable to moisture is located between said inner and outer walls.

15. An electrochemical gas sensor in accordance with claim 14, wherein:

said moisture reservoir means includes hygroscopic substances in said helically wound tube.

16. An electrochemical gas sensor in accordance with claim 13, wherein:

said inner wall includes a moisture permeable tube, an inside of said tube surrounding said gas diffusion path;

said moisture reservoir means includes a helically wound tube formed of material permeable to moisture, said helically wound tube being positioned between said inner and outer walls, said outer wall being substantially moisture impermeable.

17. An electrochemical gas sensor in accordance with claim 13, wherein:

said moisture reservoir means includes hygroscopic substances positioned between said inner and outer walls.

* * * * *